United States Patent
Joshi et al.

(10) Patent No.: US 11,066,426 B2
(45) Date of Patent: Jul. 20, 2021

(54) METHODS OF MAKING POROUS MOLECULAR STRUCTURES

(71) Applicant: Georgia Tech Research Corporation, Atlanta, GA (US)

(72) Inventors: Jayraj Nayan Joshi, Atlanta, GA (US); Colton Michael Moran, Atlanta, GA (US); Krista S. Walton, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 282 days.

(21) Appl. No.: 16/293,038

(22) Filed: Mar. 5, 2019

(65) Prior Publication Data

US 2019/0270760 A1    Sep. 5, 2019

Related U.S. Application Data

(60) Provisional application No. 62/638,439, filed on Mar. 5, 2018.

(51) Int. Cl.
| | |
|---|---|
| *C07F 5/06* | (2006.01) |
| *B05D 1/32* | (2006.01) |
| *B05D 5/00* | (2006.01) |
| *B01J 20/22* | (2006.01) |
| *B01J 31/16* | (2006.01) |

(52) U.S. Cl.
CPC .............. *C07F 5/069* (2013.01); *B05D 1/32* (2013.01); *B05D 5/00* (2013.01); *B01J 20/226* (2013.01); *B01J 31/1691* (2013.01)

(58) Field of Classification Search
CPC ...... C07C 51/418; C07C 63/28; B01J 20/226; B01J 31/1691; B05D 1/32; B05D 5/00; C07F 5/069
See application file for complete search history.

(56) References Cited

PUBLICATIONS

Li et al., Chem. Eur. J. 2015, 21, 6913-6920.*
Falcaro et al., Chem. Soc. Rev. 2014, 43, 5513-5560.*
Lopez et al., Journal of the Air & Waste Management Association, 51:6, 903-912, (2001).*

* cited by examiner

*Primary Examiner* — James M Mellott
(74) *Attorney, Agent, or Firm* — Troutman Pepper Hamilton Sanders LLP; Ryan Schneider; Dustin Weeks

(57) ABSTRACT

Disclosed herein is a method of making a porous molecular structure from a solution comprising an insoluble metal containing material and a ligand-providing material. In some embodiments, the porous molecular structure can be a Metal-Organic Framework (MOF). Ionic metal salts are the most common type of metal source for MOF production, but dissolution of metal salts complicates solvent recycling and creates corrosion and oxidation issues through evolved nitrate and chloride anions. Elucidating information that leads toward more efficient production of these versatile nanomaterials, while extending the knowledge base of how MOFs form during reaction, is critical to advancing MOF materials into large-scale use. Disclosed herein are improved methods for controlled synthesis of porous molecular structures such as MOFs comprising a solution-based synthesis with insoluble metallic precursor.

20 Claims, 7 Drawing Sheets

METHODS OF MAKING POROUS MOLECULAR STRUCTURES

CROSS-REFERENCE TO RELATED APPLICATIONS

This application claims the benefit, under 35 U.S.C. § 119(e), of U.S. Provisional Patent Application No. 62/638,439, filed 5 Mar. 2018, the entire contents and substance of which is incorporated herein by reference in its entirety as if fully set forth below.

STATEMENT OF RIGHTS UNDER FEDERALLY SPONSORED RESEARCH

This invention was made with government support under Grant No. DE-SC0012577 awarded by the U.S. Department of Energy. The government has certain rights in the invention.

FIELD OF THE DISCLOSURE

The present disclosure relates generally to molecular structures and methods of improving the same. Particularly, embodiments of the present disclosure relate to porous molecular frameworks.

BACKGROUND

Metal-Organic Frameworks (MOFs) are well-known for their large surface areas, tunable ligand moieties, and reactive open metal sites. In general, MOFs are obtained through solution reactions between organic ligands and soluble metal salts in polar solvents. Ionic metal salts are the most common type of metal source for MOF production, but dissolution of metal salts complicates solvent recycling and creates corrosion and oxidation issues through evolved nitrate and chloride anions. Elucidating information that leads toward more efficient production of these versatile nanomaterials, while extending the knowledge base of how MOFs form during reaction, is critical to advancing MOF materials into large-scale use. In pursuit of controlled MOF crystal growth, a myriad of research studies have developed around the area of layer-by-layer growth mechanisms with self-assembled monolayers on noble metal substrates. These techniques allow for monolayer control through synthesis procedures that rely on cyclic exposures to metal salts and linkers with intermittent rinsing steps. However, the problem of dissolution of the metal salt in the solvent still remains. Thus, other methods that simplify the synthesis process for controlling MOF growth and enable scale-up to industry are of interest to the field.

What is needed, therefore, is a method of manufacturing a MOF or other porous molecular structure in solution which removes the corrosion and oxidation risks and provides for improved solvent recyclability and purity. Embodiments of the present disclosure address this need as well as other needs that will become apparent upon reading the description below in conjunction with the drawings.

BRIEF SUMMARY OF THE INVENTION

The present invention relates to porous molecular structures and methods for making the same. An exemplary embodiment of the present invention provides a method of making a porous molecular structure, the method comprising: mixing a metal-containing material, a ligand-providing material, and a solvent to create a mixture, wherein the metal-containing material is insoluble in the solvent; and reacting, in the mixture, the metal-containing material with the ligand-providing material to form a porous molecular structure.

In some embodiments, the method can further comprise removing, from the solution, the porous molecular structure.

In some embodiments, the metal-containing material can be an insoluble solid metallic material.

In some embodiments, the insoluble solid metallic material can be a metal carbide.

In some embodiments, the ligand-providing material can comprise an organic ligand.

In some embodiments, the porous molecular structure can be a Metal Organic Framework (MOF).

In some embodiments, the porous molecular structure can comprise all of the metal-containing material from mixture.

In some embodiments, the method can further comprise recovering at least a portion of the solvent from the mixture after the porous molecular structure is formed.

In some embodiments, the reacting can occur for 4 hours or greater at 220° C.

Another embodiment of the present disclosure provides a method of making a porous molecular structure, the method comprising: providing at least an insoluble solid metallic material, a ligand-providing material, and a solvent; mixing, by adding the ligand-providing material to the solvent, to form a mixture; contacting at least a portion of the insoluble solid metallic material with the mixture; and reacting, the metallic material with the ligand-providing material to form a porous molecular structure.

In some embodiments, the insoluble solid metallic material can be a metal carbide.

In some embodiments, the ligand-providing material can comprise an organic ligand.

In some embodiments, the porous molecular structure can be a Metal Organic Framework (MOF).

In some embodiments, the porous molecular structure can comprise all of the insoluble metallic material.

In some embodiments, the method can further comprise recovering at least a portion of the solvent from the mixture after the porous molecular structure is formed.

Another embodiment of the present invention provides a method of making a porous molecular structure, the method comprising: providing at least an insoluble solid metallic material, a ligand-providing material, and a solvent; and reacting, in the solvent, at least a portion of the insoluble solid metallic material with the ligand-providing material to form a porous molecular structure.

In some embodiments, the method can further comprise forming a solution comprising the solvent and the ligand-providing material.

In some embodiments, the reacting can comprise contacting the at least a portion of the insoluble solid metal material with the ligand-providing material.

In some embodiments, the method can further comprise masking the insoluble metal material with a nonreactive mask having a predetermined pattern.

In some embodiments, the contacting can occur at spaces formed by the predetermined pattern in the nonreactive mask.

These and other aspects of the present invention are described in the Detailed Description of the Invention below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1:
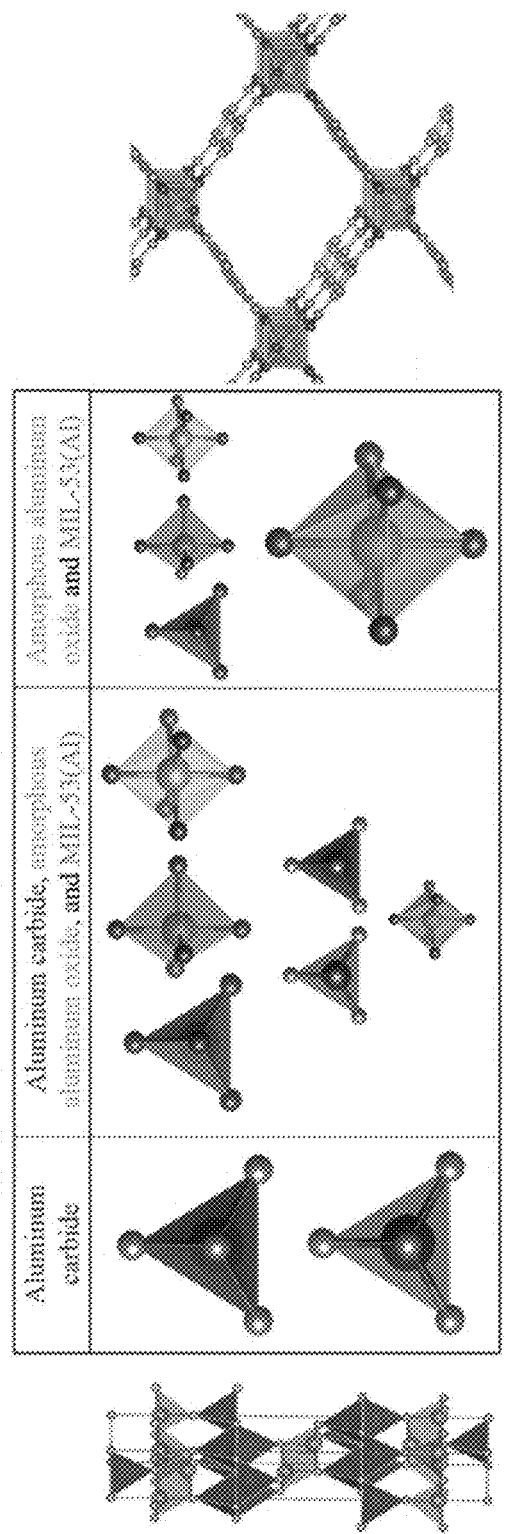
FIG. 1 shows a rendering of a structure of an exemplary embodiment of a porous molecular structure.
Figure 2:
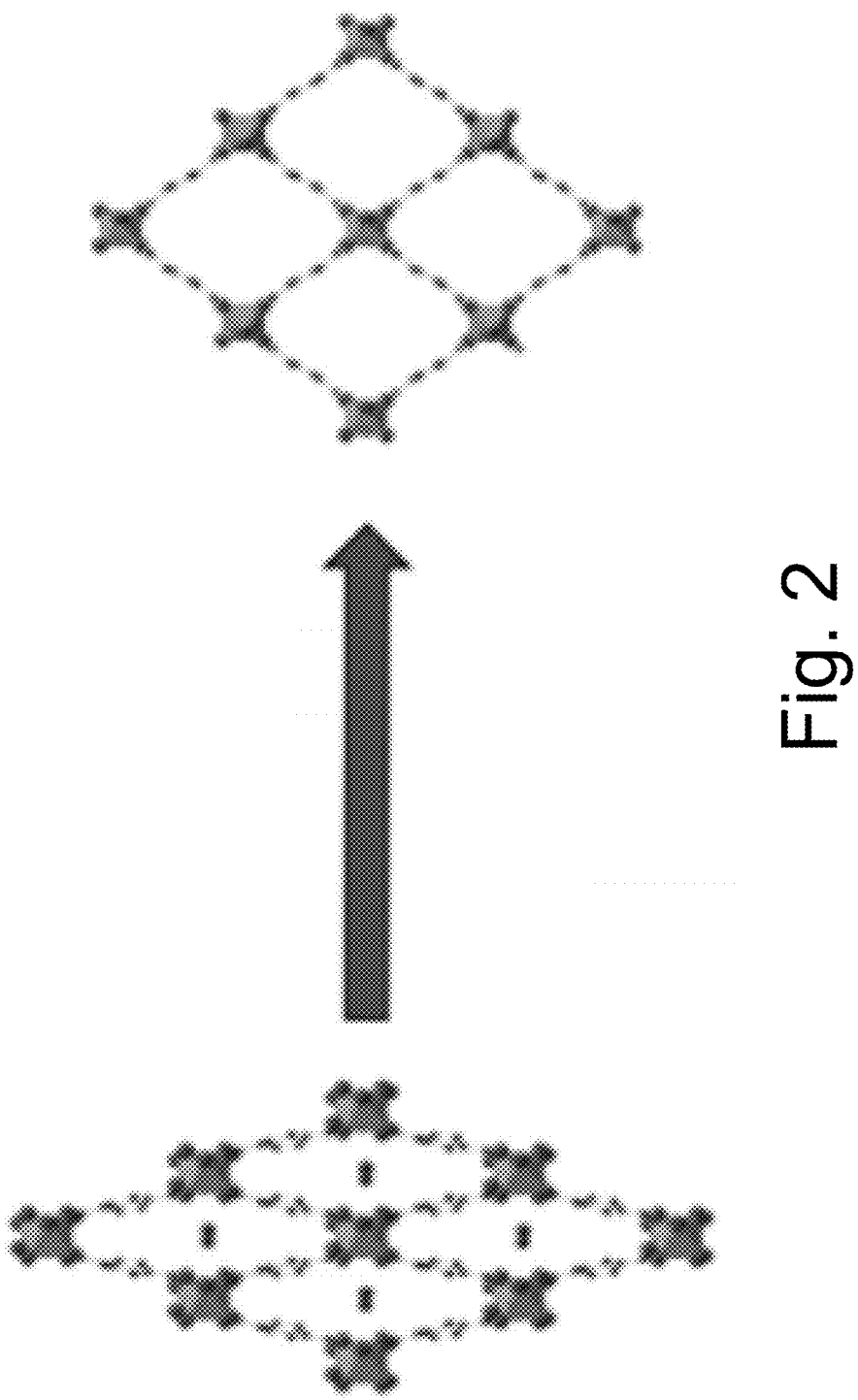
FIG. 2 shows a rendering of a structure of an exemplary embodiment of a porous molecular structure and metal-containing material.
Figure 3:
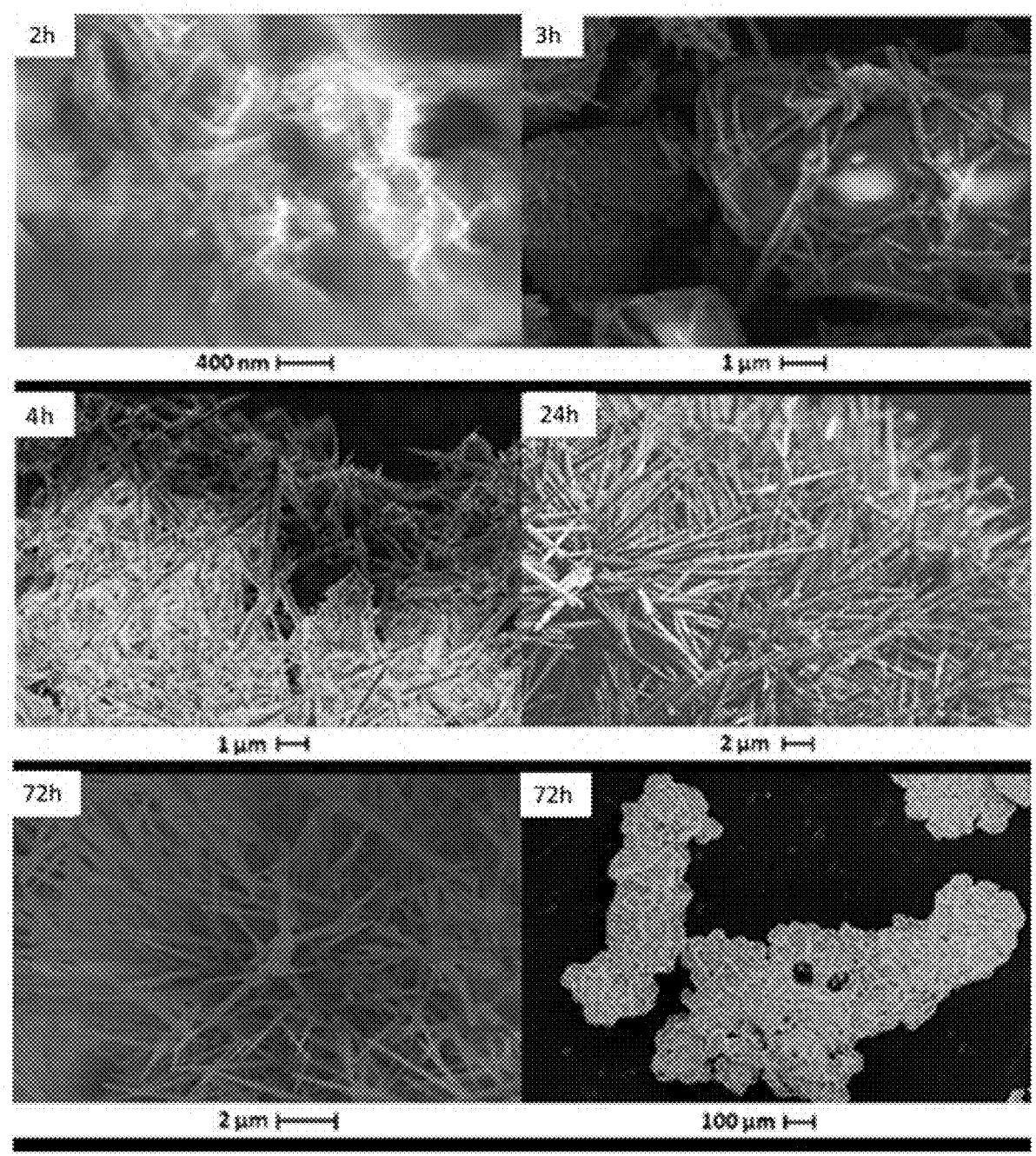
FIG. 3 shows a series of Scanning Electron Microscope (SEM) images of a porous molecular structure undergoing growth during reaction.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

As described above, a problem with current methods of manufacturing Metal-Organic Frameworks (MOFs) is the dissolution of the soluble metal precursors in the solvent, creating an impure solvent that is difficult to recycle. Additionally, the risks of corrosion and oxidation make current methods of manufacturing MOFs impractical. The use of alternative metal precursors such as metal oxides and metal hydroxides would provide a more flexible and cost-effective strategy for MOF production and would also provide a potential method for direction- and shape-controlled synthesis. Additionally, recent literature has begun to examine the growth of MOFs directly from solid precursors. The potential of MOFs and other porous molecular structure technologies has created an important technological field that shows great advancement. These structures have potential to be used in many industries, such as hydrocarbon processing, wastewater treatment, bioprocessing, gas scrubbing and adsorption, carbon capture, consumer filtration, catalysis, improved reactor kinetics, biofuels, petroleum refining, and the like. Thus, developing improved porous molecular structures, such as MOFs, with methods of manufacture easily scalable to large industry sizes would greatly extend the design space and industrial capabilities of this technology.

When studying the growth of such structures from solid precursors, attention is turned to metal carbides. Metal carbides are crystalline materials comprised of metal-carbon bonds and include a large number of transition metals. Binary and ternary carbides also provide a variety of potential mixed metal systems to be explored. Recent developments in green and economical carbide production have produced high purity carbides on the time scale of seconds to minutes using elemental precursors, adding to their viability as an alternative solid precursor.

Disclosed herein is a method of making a porous molecular structure. A porous molecular structure can be many structures, including but not limited to, metal-organic frameworks (MOFs), zeolites, carbon molecular sieves, polyimide membranes, hollow fiber membranes, dense film membranes, mixed matrix membranes, and the like. Methods of manufacture utilizing solid insoluble precursors in solution are desirable due to improvements in solvent recyclability and reduced risk of corrosion. According to some embodiments of the present disclosure, the use of insoluble metal-containing materials to foster directed growth of MOFs in a solution with a ligand-providing material was demonstrated. Such embodiments can use metal-carbon matrices such as metal carbide materials. A unique needle-like morphology of the MOF was grown parallel to the bulk solid surface in a layer-by-layer manner. The synthesis scheme was found to be transferrable to the production of different linker analogs of the MOF and other topologies. Given the variety of metal carbides available, the present disclosure can be used as a blueprint for controlled, efficient, and economical MOF synthesis methods and improve the state of the art toward the industrial use of porous molecular structures at large scale.

Disclosed herein are methods of making porous molecular structures. Suitable examples of porous molecular structures can include, but are not limited to, zeolites, MOFs, porous organic cages, a combination thereof, or any other molecular framework. Embodiments of the present disclosure can provide an insoluble metal-containing precursor material. In some embodiments, the insoluble metal-containing precursor material can comprise an insoluble solid metallic material. In some embodiments, the insoluble solid metallic material can comprise a metal carbide. For example, the insoluble solid metallic material can be a block of solid aluminum carbide. In other embodiments, the insoluble solid metallic material can comprise any metal carbide, such as titanium carbide, zirconium carbide, vanadium carbide, chromium carbide, iron carbide, manganese carbide, cobalt carbide, nickel carbide, metal carbido complexes, metallo-carbohedrynes, and the like. In some embodiments, the metal-containing material can comprise any insoluble solid material containing elemental metallic elements for a desired porous molecular structure. For example, if the desired porous molecular structure is the aluminum-based MIL-53, the metal-containing material can be any solid insoluble aluminum-containing material, such as pure aluminum, aluminum cans, aluminum foil, and the like. Likewise, if the desired porous molecular structure is copper-based, for instance, the metal-containing material can be any solid insoluble copper-containing material, such as pennies, coins, copper wire, copper tape, copper mesh, pure copper, copper carbide, and the like.

In some embodiments, the insoluble metal-containing material can undergo a reaction to form a porous molecular structure. Embodiments of the present disclosure can provide a ligand-providing material for reaction with the insoluble metal-containing material. In some embodiments, the ligand-providing material can be an organic ligand. Suitable examples of ligand-providing materials can include, but are not limited to iodide, bromide, sulfide, thiocyanate, chloride, nitrate, azide, fluoride, hydroxide, oxalate, aqua, water, nitrile, isothiocyanate, acetonitrile, pyridine, ammonia, ethylenediamine, bipyridine, phenanthroline, nitrite, triphenylphosphine, cyanide, carbon monoxide, acetylacetonate, alkenes, amino polycarboxylic acids, benzene, bis(diphenylphosphino) ethane, bis(diphenylphosphino) methane, corroles, crown ethers, cryptand, cryptates, cyclopentadienyl, diethylenetriamine, dimethyl glyoximate, pentetic acid, ethylenediamine tetraacetic acid, ethylenediamine tetraacetate, fura-2, glycinate, heme, iminodiacetic acid, nitrosyl, nitrilotriacetic acid, oxo, pyrazine, scorpionate ligand, sulfite, terpyridine, triazacyclononane, tricyclohexylphosphine, triethylenetetramine, trimethylphosphine, tropylium, carbon dioxide, phosphorus triflouoride, a combination thereof, and the like. Other embodiments can comprise ligand-providing materials known to one of ordinary skill in the art, or ligand-providing materials known to produce a predetermined porous molecular structure.

Embodiments of the present disclosure can provide a solvent. The solvent compound can be any substance able to dissolve substantially dissolve the ligand-providing material to create a liquid solution at room temperature and pressure. Suitable examples of a solvent can include, but are not limited to, nonpolar solvents, polar aprotic solvents, polar protic solvents, water-miscible solvents, or a combination thereof. There are many examples of appropriate solvents known to one of ordinary skill in the art, but suitable examples can include, but are not limited to, acetaldehyde, acetic acid, acetone, acetonitrile, butanediol, butoxyethanol, butyric acid, diethanolamine, diethylenetriamine, dimethyl acetamide (DMAc), dimethylformamide (DMF), dimethoxy ethane, dimethyl sulfoxide (DMSO), dioxane, ethanol, ethylamine, ethylene glycol, formic acid, furfuryl alcohol, glycerol, methanol, methyl diethanolamine, methyl isocyanide, N-methyl-2-pyrrolidone (NMP), propanol, propanediol, propanoic acid, propylene glycol, pyridine, tetrahydrofuran (THF), triethylene glycol, dimethyl hydrazine, hydrazine, hydrofluoric acid, hydrogen peroxide, nitric acid, sulfuric acid, pentane, cyclopentane, hexane, cyclohexane, benzene, toluene, chloroform, diethyl ether, dichloromethane, or a combination thereof. As would be appreciated by one of ordinary skill in the art, the solvent can be selected from any substance able to dissolve the desired ligand-providing material at room temperature and pressure.

There exist many methods for determining level of solubility of the ligand-providing material in the solvent. In some embodiments, the Hildebrand solubility parameters can be determined for the ligand-providing material and the solvent. In some embodiments, the Hildebrand solubility parameters can have a difference of 3.6 MPa$^{1/2}$ or less. As would be appreciated by one of ordinary skill in the art, such an embodiment would provide a solvent which would be able to dissolve the ligand-providing material to create a substantially homogeneous solution.

In some embodiments, the solvent is substantially unable to dissolve the metal-containing material. In some embodiments, the weight ratio of the solvent is present in an amount such that metal-containing material dissolves at room temperature and pressure in an amount of 1% or less (e.g., 0.9% or less, 0.8% or less, 0.7% or less, 0.6% or less, 0.5% or less, 0.4% or less, 0.3% or less, 0.2% or less, or 0.1% or less) by weight based on total weight of the solution to form a homogeneous solution. In some embodiments, the Hansen solubility parameters can be determined for the metal-containing material and the solvent. In some embodiments, the Relative Energy Difference calculated from the Hansen solubility parameters of the metal-containing material and the solvent can be 1 or greater. As would be appreciated by one of ordinary skill in the art, such an embodiment would provide a solvent which would be unable to dissolve the metal-containing material.

In some embodiments, the reaction an occur in a solution with a solvent. In other embodiments, the reaction can occur by contacting the ligand-providing material in a solvent with the insoluble metal-containing material. In some embodiments, a solution is formed comprising the ligand-providing material and the solvent before contacting the solution with the metal-containing material.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

Figure 4:
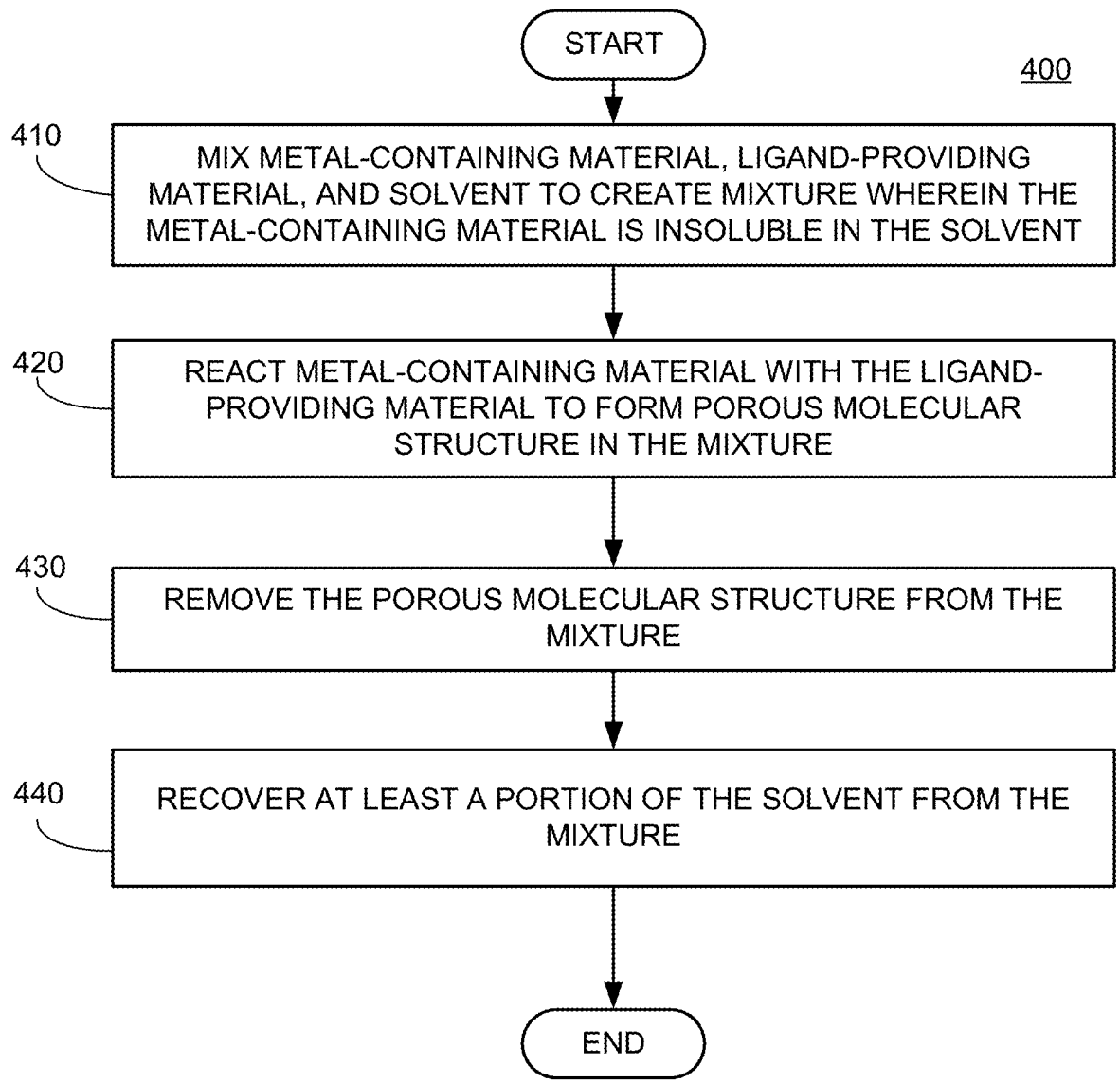
FIG. 4 is a flowchart of an exemplary method for making a porous molecular structure.
Figure 5:
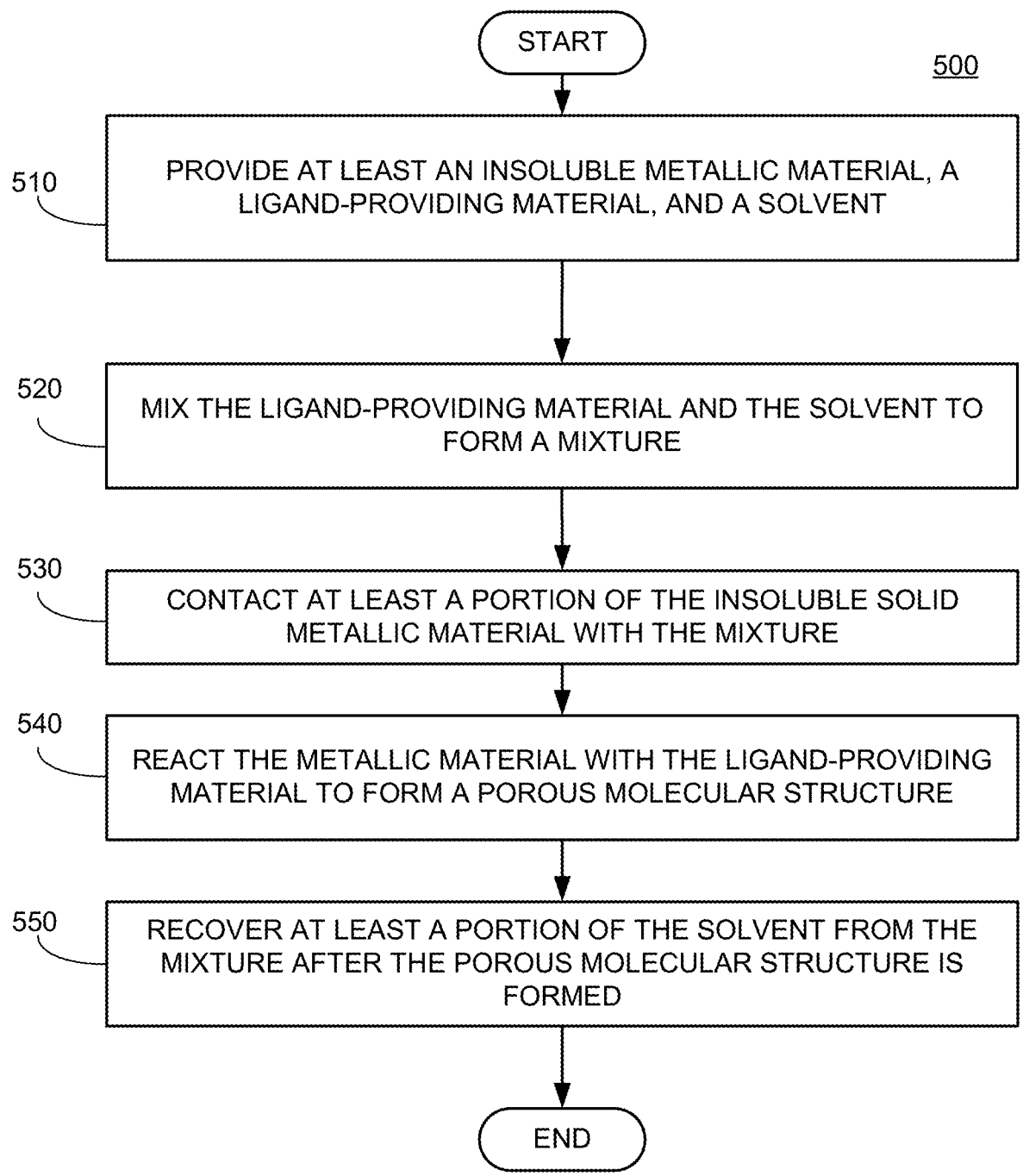
FIG. 5 is a flowchart of an exemplary method for making a porous molecular structure.
Figure 6:
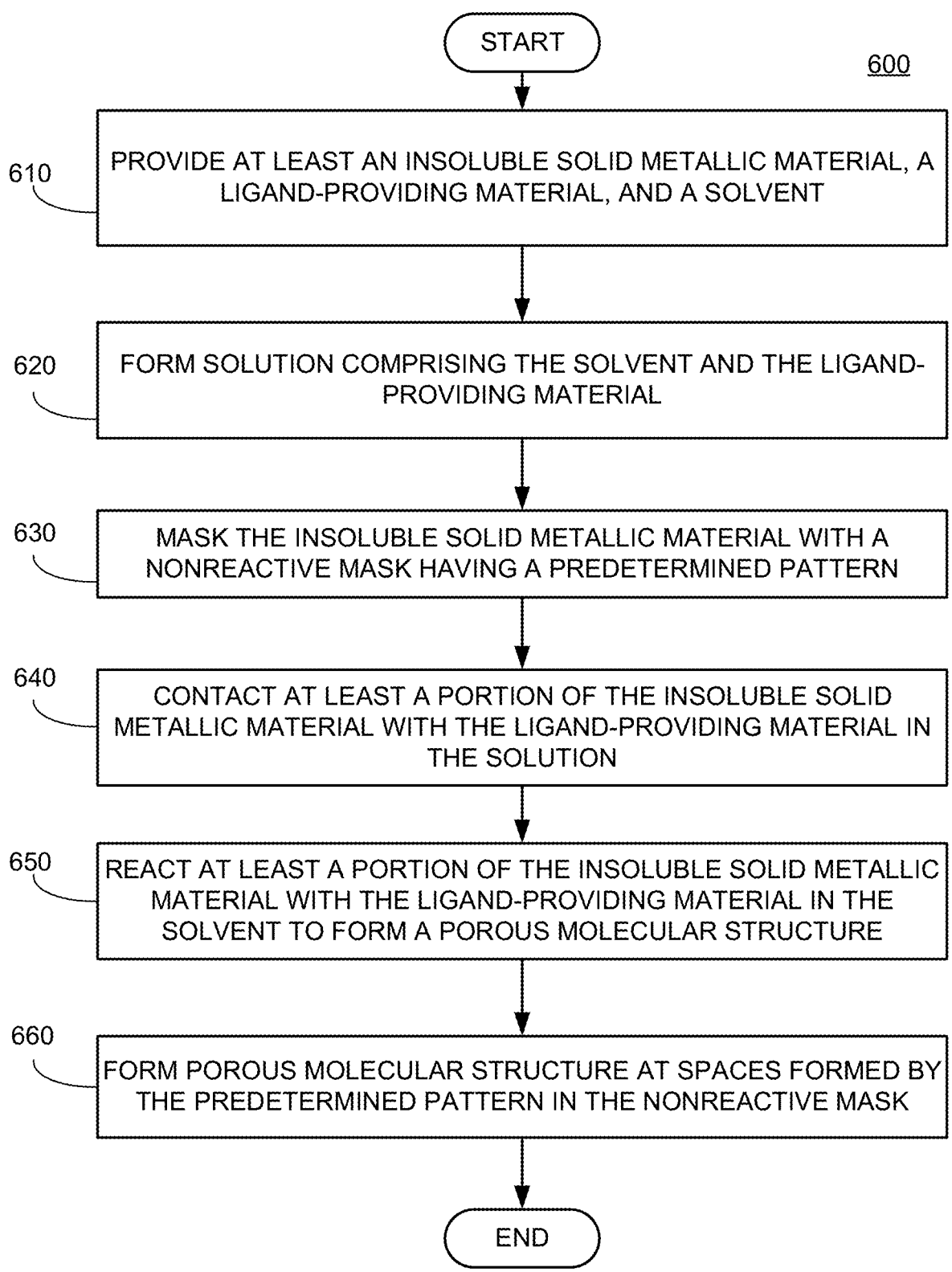
FIG. 6 is a flowchart of an exemplary method for making a porous molecular structure.
Figure 7:
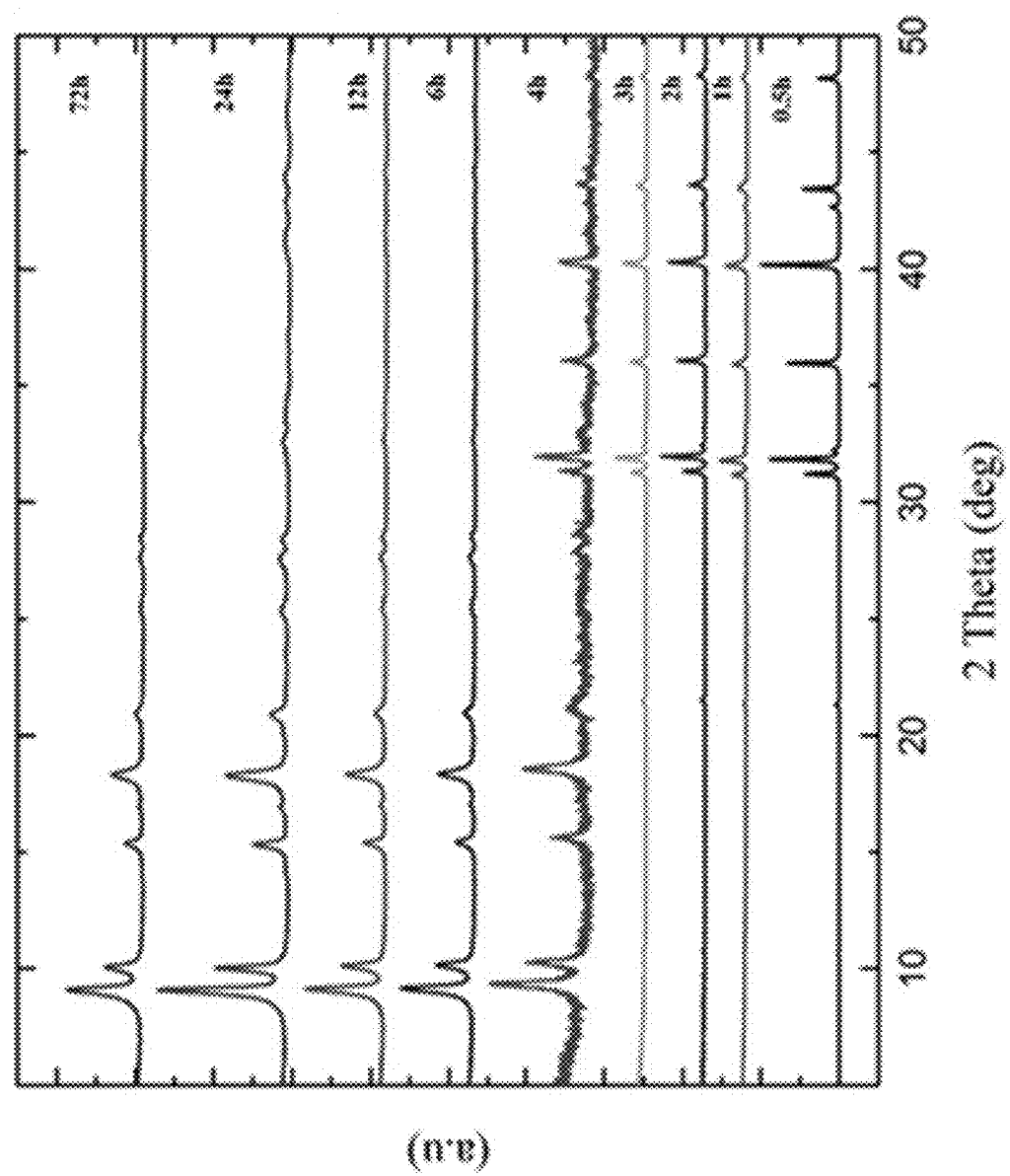
FIG. 7 shows a powder x-ray diffraction shift for an exemplary embodiment of a porous molecular structure and metal-containing material during reaction.

FIGS. 4-6 illustrate exemplary embodiments of the presently disclosed method.

In FIG. 4, a method for making a porous molecular structure is disclosed herein. In block 410, a provided metal-containing material, ligand-providing material, and solvent can be mixed to create a mixture wherein the metal-containing material is insoluble in the solvent. In some embodiments, the mixture can be mixed using sonication. Other methods of mixing are contemplated, such as agitation, magnetic stir bars, rollers, and the like. It is understood that, in some embodiments, the mixture can comprise other species, such as inhibitors, catalysts, nonsolvents, and the like.

In block 420, the mixture can undergo a reaction between the metal-containing material and the ligand-providing material to form a porous molecular structure. In some embodiments, the reaction can comprise a layer-by-layer process. In other words, the reacting process comprises forming the porous molecular structure on the surface of the metal-containing material in layers. In some embodiments, the porous molecular structure can comprise a needle-like morphology during growth. In some embodiments, the reacting can occur for 4 hours or greater (e.g., 5 hours or greater, 6 hours or greater, 7 hours or greater, 8 hours or greater, 9 hours or greater, 10 hours or greater, 12 hours or greater, 15 hours or greater, 20 hours or greater, 24 hours or greater, 30 hours or greater, 40 hours or greater, 50 hours or greater, 60 hours or greater, 70 hours or greater, or 72 hours or greater). In some embodiments, the porous molecular structure can comprise all of the metal-containing material. In other words, a complete consumption of the metal-containing material precursor can be observed during the reaction, leaving no remnants of the metal-containing material precursor after the formation of the porous molecular structure. In some embodiments, the reacting can occur at 180° C. or greater (e.g., 190° C. or greater, 200° C. or greater, 210° C. or greater, 220° C. or greater, 230° C. or greater, 240° C. or greater, or 250° C. or greater). In some embodiments, the reacting can occur at 250° C. or less (e.g., 240° C. or less, 230° C. or less, 220° C. or less, 210° C. or less, 200° C. or less, 190° C. or less, or 180° C. or less). In some embodiments, the reacting can occur at from 180° C. to 250° C. (e.g., from 180° C. to 190° C., from 190° C. to 200° C., from 200° C. to 210° C., from 210° C. to 220° C., from 220° C. to 230° C., from 230° C. to 240° C., or from 240° C. to 250° C.). In some embodiments, the reacting can occur in an autoclave, or other fixed volume vessel. In some embodiments, the reacting can occur without a significant temperature change.

In block 430, the porous molecular structure can be removed from the mixture. In some embodiments, the porous molecular structure can be washed and/or submerged in one or more solvents to remove excess materials. In some embodiments, the porous molecular structure can be washed and/or submerged in one or more nonsolvents to remove excess solvent. In some embodiments, the porous molecular structure can be dried further. By way of example, a porous molecular structure can be submerged in DMF after the reaction to remove excess ligand-providing material, and further submerged in methanol to remove excess DMF. In other examples, the porous molecular structure can be dried in a fume hood, oven, convection oven, vacuum oven, or the like.

In block 440, at least a portion of the solvent in the mixture can be recovered. In some embodiments, the solvent can be substantially pure. Due to the insolubility of the metallic material and the complete conversion of metallic precursor to porous molecular structure, the solvent can remain substantially free of impurities. In some embodiments, the porous molecular structure can be removed from the mixture and a new insoluble solid metallic material can be added to the mixture to start another reaction.

In FIG. 5, a method for making a porous molecular structure is disclosed herein. In block 510, an insoluble solid metallic material, ligand-providing material, and solvent can be provided.

In block 520, a provided insoluble solid metallic material, ligand-providing material, and solvent can be mixed to create a mixture wherein the insoluble solid metallic material is insoluble in the solvent. In some embodiments, the mixture can be mixed using sonication. Other methods of mixing are contemplated, such as agitation, magnetic stir bars, rollers, and the like. It is understood that, in some embodiments, the mixture can comprise other species, such as inhibitors, catalysts, nonsolvents, and the like.

In block 530, at least a portion of the insoluble solid metallic material can be contacted by the mixture. In some embodiments, the mixture can be contacted with the metallic material by pouring, pipetting, submerging, wiping, and other methods sufficient to bring the insoluble solid metallic material in contact with the mixture.

In block 540, the mixture can undergo a reaction between the insoluble solid metallic material and the ligand-providing material to form a porous molecular structure. In some embodiments, the reaction can comprise a layer-by-layer process. In other words, the reacting process comprises forming the porous molecular structure on the surface of the insoluble solid metallic material in layers. In some embodiments, the porous molecular structure can comprise a needle-like morphology during growth. In some embodiments, the reacting can occur for 4 hours or greater (e.g., 5 hours or greater, 6 hours or greater, 7 hours or greater, 8 hours or greater, 9 hours or greater, 10 hours or greater, 12 hours or greater, 15 hours or greater, 20 hours or greater, 24 hours or greater, 30 hours or greater, 40 hours or greater, 50 hours or greater, 60 hours or greater, 70 hours or greater, or 72 hours or greater). In some embodiments, the porous molecular structure can comprise all of the insoluble solid metallic material. In other words, a complete consumption of the insoluble solid metallic precursor can be observed during the reaction, leaving no remnants of the insoluble solid metallic precursor after the formation of the porous molecular structure. In some embodiments, the reacting can occur at 180° C. or greater (e.g., 190° C. or greater, 200° C. or greater, 210° C. or greater, 220° C. or greater, 230° C. or greater, 240° C. or greater, or 250° C. or greater). In some embodiments, the reacting can occur at 250° C. or less (e.g., 240° C. or less, 230° C. or less, 220° C. or less, 210° C. or less, 200° C. or less, 190° C. or less, or 180° C. or less). In some embodiments, the reacting can occur at from 180° C. to 250° C. (e.g., from 180° C. to 190° C., from 190° C. to 200° C., from 200° C. to 210° C., from 210° C. to 220° C., from 220° C. to 230° C., from 230° C. to 240° C., or from 240° C. to 250° C.). In some embodiments, the reacting can occur in an autoclave, or other fixed volume vessel. In some embodiments, the reacting can occur without a significant temperature change.

In block 550, at least a portion of the solvent in the mixture can be recovered. In some embodiments, the solvent can be substantially pure. Due to the insolubility of the metallic material and the complete conversion of metallic precursor to porous molecular structure, the solvent can remain substantially free of impurities.

In FIG. 6, a method for making a porous molecular structure is disclosed herein. In block 610, an insoluble solid metallic material, ligand-providing material, and solvent can be provided.

In block 620, a provided ligand-providing material and solvent can be mixed to create a solution wherein the insoluble solid metallic material is insoluble in the solution. In some embodiments, the solution can be mixed using sonication. Other methods of mixing are contemplated, such as agitation, magnetic stir bars, rollers, and the like. It is understood that, in some embodiments, the solution can comprise other species, such as inhibitors, catalysts, non-solvents, and the like.

In block 630, a mask can be provided to substantially enclose or surround the insoluble solid metallic material. In some embodiments, the mask can comprise plastic, a polymer, a separate insoluble metal, or any species so long as the mask is nonreactive when in contact with the solution. The mask can comprise any predetermined or functional pattern to control the growth of the porous molecular structure. For example, the mask can comprise dots or holes uniformly dispersed to allow for structure growth from the predetermined holes.

In block 640 at least a portion of the insoluble solid metallic material can be contacted by the mixture. In some embodiments, the mixture can be contacted with the metallic material by pouring, pipetting, submerging, wiping, and other method sufficient to bring the insoluble solid metallic material in contact with the mixture.

In block 650, the mixture can undergo a reaction between the insoluble solid metallic material and the ligand-providing material to form a porous molecular structure. In some embodiments, the reaction can comprise a layer-by-layer process. In other words, the reacting process comprises forming the porous molecular structure on the surface of the insoluble solid metallic material in layers. As would be appreciated by one of ordinary skill in the art, such an embodiment would provide layer-by-layer growth in areas designated to be reacted by the mask. In some embodiments, the porous molecular structure can comprise a needle-like morphology during growth. In some embodiments, the reacting can occur for 4 hours or greater (e.g., 5 hours or greater, 6 hours or greater, 7 hours or greater, 8 hours or greater, 9 hours or greater, 10 hours or greater, 12 hours or greater, 15 hours or greater, 20 hours or greater, 24 hours or greater, 30 hours or greater, 40 hours or greater, 50 hours or greater, 60 hours or greater, 70 hours or greater, or 72 hours or greater). In some embodiments, the porous molecular structure can comprise all of the insoluble solid metallic material. In other words, a complete consumption of the insoluble solid metallic precursor can be observed during the reaction, leaving no remnants of the insoluble solid metallic precursor after the formation of the porous molecular structure. In other embodiments, the insoluble solid metallic material can act as a substrate for the predetermined pattern of growth set by the mask. In some embodiments, the reacting can occur at 180° C. or greater (e.g., 190° C. or greater, 200° C. or greater, 210° C. or greater, 220° C. or greater, 230° C. or greater, 240° C. or greater, or 250° C. or greater). In some embodiments, the reacting can occur at 250° C. or less (e.g., 240° C. or less, 230° C. or less, 220° C. or less, 210° C. or less, 200° C. or less, 190° C. or less, or 180° C. or less). In some embodiments, the reacting can occur at from 180° C. to 250° C. (e.g., from 180° C. to 190° C., from 190° C. to 200° C., from 200° C. to 210° C., from 210° C. to 220° C., from 220° C. to 230° C., from 230° C. to 240° C., or from 240° C. to 250° C.). In some embodiments, the reacting can occur in an autoclave, or other fixed volume vessel. In some embodiments, the reacting can occur without a significant temperature change.

Reference will now be made in detail to exemplary embodiments of the disclosed technology, examples of which are illustrated in the accompanying drawings and disclosed herein.

EXAMPLES

The following examples are provided by way of illustration but not by way of limitation.

Example 1

Methods

MIL-53(Al) analogues were prepared using a 3:1 organic linker to aluminum molar ratio. 50 mg of aluminum carbide (Al4C3, Strem Chemicals 98% purity 325 mesh) and 693 mg of terephthalic acid (C4H4(COOH)2, Sigma Aldrich 98% purity), referred to as BDC hereafter, were placed in a 20 mL Teflon-lined stainless-steel reactor. 7.5 mL of N,N-dimethylformamide (C3H7NO, Sigma Aldrich 98% purity), referred to as DMF hereafter, was added to the mixture, and the reagents were agitated via sonication for 5 minutes. The reactor was then sealed and placed in a preheated isothermal oven at 220° C., unless stated otherwise, for the entirety of the predetermined reaction time. The reactor was then removed from the oven and cooled in ambient air. The resulting liquid-solid mixture was gravity-filtered and washed three times with DMF and then methanol. In some cases, the reaction mixture was decanted, and the liquid portion was stored for further analysis.

Example 2

Materials and Methods

Reynolds Wrap® brand aluminum foil was purchased from a local grocery store in Atlanta, Ga. No pretreatment of the foil was performed prior to reaction. Foil squares of approximately 50 mg were cut and placed into reactors prior to MOF syntheses. 200 mesh (0.0021" wire diameter) samples were purchased from TWP Inc. Samples were received as 3"×3" pieces but cut into smaller squares to allow the mesh to fit into reactors. After reaction, tweezers were used to recover mesh-MOF composites from the reaction mixture.

Terephthalic acid (≥98% purity) and 2-aminoterephthalic acid (≥99+% purity) were purchased from Sigma Aldrich and used with no further purification to create MIL-53(Al) and MIL-53-NH$_2$(Al) samples, respectively. Trimesic acid (95% purity) from Sigma Aldrich was used without further purification.

Aluminum foil (1.8 mmol, 50 mg) and terephthalic acid (5.56 mmol, 924 mg) were added in a 1:3 molar ratio to deionized (DI) water (555 mmol, 10 mL). The ratio of ligand-to-solvent was approximately 0.556 mmol of ligand per mL of water. The foil was placed as a small square (approx. 1"×1") into the reaction vessel. The solution was sonicated at ambient temperature for 5 min to partially dissolve the terephthalic acid into solution. The reagent mixture was then transferred to a 20 mL PTFE lined stainless steel autoclave. The sealed reaction vessel was transferred into a preheated oven, and held isothermally at 220° C. for 24 hours, and allowed to cool naturally afterwards. The product was carefully recovered from the autoclaves post-reaction with tweezers, and submerged into N,N-dimethylformamide (DMF), under gentle agitation, for at least 5 min to remove uncoordinated ligands. The product was then submerged in fresh methanol to remove the DMF for at least 10 min. Composite pieces were allowed to dry first in a well-ventilated chemical hood overnight. Degassing was performed at 150° C. for 24 h under vacuum.

Aluminum foil (1.8 mmol, 50 mg) was first shredded by hand into small pieces (approximately 1"×1"). The foil was placed in a PTFE reactor, along with terephthalic acid (5.56 mmol, 924 mg) in a 1:3 aluminum-to-ligand molar ratio. Deionized (DI) water (555 mmol, 10 mL) was also placed in the reaction, making a ratio of 0.556 mmol ligand per 1 mL of solvent. The solution was sonicated for 5 min to partially dissolve the coordinating ligands in the aqueous solution. Under a chemical hood, concentrated hydrochloric acid (HCl, 36% w/w) from Alfa Aesar was added to the reaction mixture using a micropipette to create the various molar concentrations of HCl(aq). For the optimized 0.5M HCl reaction, 4.96 mmol (152 µL) of concentrated HCl(aq) was added. The reactor was then quickly sealed and placed in a preheated oven. Different synthesis temperatures and times were utilized, as described above; all reactions were carried out isothermally. After reaction, the autoclave was cooled naturally in a chemical hood. The resulting solids were filtered, washed three times with both DMF and then methanol, and allowed to dry overnight under ambient conditions. Degassing of dry samples was conducted under vacuum at 150° C. for 24 hours.

Example 3

Characterization Methods

An X-Pert Pro PANalytical X-ray diffractometer was used to collect PXRD measurements, with a Cu Kα ($\lambda$=1.542 Å) X-ray source. All samples were rotated during data collection. Solid samples were secured flush to a low-background sample holder. Powder samples were placed homogenously into wells on low-background sample holders. For MIL-53(Al) containing samples and aluminum samples, a range of from 2θ=4°-45° with 0.02° step size was used; for MIL-96(Al)/MIL-100(Al) samples, 2θ=2°-45° with a step size of 0.01° was used; for non-framework alumina materials, 2θ=10°-70° with a step size of 0.02° was used.

Several microscopes were utilized to collect presented SEM images. Regardless of the microscope, all samples were dispersed directly onto carbon tape prior to analysis. Additionally, accelerating voltage ranges from 3-10 keV were utilized when imaging materials.

A Zeiss Ultra60 Field Emission (FE) SEM was utilized to image aluminum foil/mesh-MOF composites, as well as non-supported MIL-53(Al) and MIL-96(Al) samples. EDS mapping was additionally performed using the Zeiss microscope, within a range of 5-10 keV.

Nitrogen sorption measurements at 77 K were obtained using a Quantachrome Quadrasorb SI volumetric analyzer. Isotherms were collected at 77 K using a sample of 50-75 mg. Prior to each isotherm, the sample was outgassed for approximately 18 hours at 150° C. and under vacuum (approximately 20 mTorr). Specific surface areas were calculated using the BET model in the relative pressure range ($P/P_0$) 0.005-0.03.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. A method comprising:
    masking a metal-containing material with a nonreactive mask having a predetermined pattern;
    mixing the masked metal-containing material, a ligand-providing material, and a solvent in which the metal-containing material and the mask are insoluble, forming a mixture; and
    reacting, in the mixture, the masked metal-containing material with the ligand-providing material, forming a porous molecular structure.

2. The method of claim 1 further comprising removing, from the mixture, the porous molecular structure.

3. The method of claim 1, wherein the metal-containing material is an insoluble solid metallic material.

4. The method of claim 3, wherein the insoluble solid metallic material is a metal carbide.

5. The method of claim 1, wherein the ligand-providing material comprises an organic ligand.

6. The method of claim 1, wherein the porous molecular structure is a Metal Organic Framework (MOF).

7. The method of claim 1, wherein the porous molecular structure comprises all of the metal-containing material from the mixture.

8. The method of claim 1 further comprising recovering at least a portion of the solvent from the mixture after the porous molecular structure is formed.

9. The method of claim 1, wherein the reacting occurs for four hours or greater at 220° C.

10. The method of claim 1, wherein reaction of the masked metal-containing material with the ligand-providing material occurs at spaces formed by the predetermined pattern in the nonreactive mask.

11. A method comprising:
    mixing an organic ligand-providing material with a solvent;
    masking a metal carbide with a nonreactive mask having a predetermined pattern; and
    adding the masked metal carbide to the mixture of the organic ligand-providing material and the solvent;
    wherein the metal carbide and the mask are insoluble in the solvent; and
    whereupon reaction of the masked metal carbide with the organic ligand-providing material forms a porous molecular structure.

12. The method of claim 11, wherein the porous molecular structure is a Metal Organic Framework (MOF).

13. The method of claim 11 further comprising recovering at least a portion of the solvent after the porous molecular structure is formed.

14. The method of claim 11, wherein reaction of the masked metal carbide with the organic ligand-providing material occurs at spaces formed by the predetermined pattern in the nonreactive mask.

15. A one-step method comprising reacting for a time period a masked metal-containing material with a solution comprising a solvent and a ligand-providing material;
    wherein the mask of the masked metal-containing material is a nonreactive mask having a predetermined pattern;

wherein the metal-containing material and the mask are insoluble in the solvent;

wherein a Metal Organic Framework (MOF) is formed upon the reacting;

wherein, when the time period is twelve hours, a Brunauer-Emmett-Teller (BET) surface area of the MOF is a twelve-hour BET surface area;

wherein, when the time period is seventy-two hours, the BET surface area of the MOF is a seventy-two-hour BET surface area; and wherein the twelve-hour BET surface area is at least 90% of the seventy-two-hour BET surface area.

16. The method of claim 15, wherein the twelve-hour BET surface area is at least 94% of the seventy-two-hour BET surface area.

17. The method of claim 15, wherein the metal-containing material is a metal carbide.

18. The method of claim 15, wherein the ligand-providing material comprises an organic ligand.

19. The method of claim 15, wherein the solvent is a non-aqueous solvent.

20. The method of claim 15, wherein reaction of the masked metal-containing material with the ligand-providing material occurs at spaces formed by the predetermined pattern in the nonreactive mask.

* * * * *